(12) United States Patent
McGee et al.

(10) Patent No.: US 9,398,964 B2
(45) Date of Patent: Jul. 26, 2016

(54) DEVICE FOR SECURING A PROSTHESIS TO THE INTERNAL WALL OF A BODY LUMEN

(75) Inventors: Graham McGee, Glasgow (GB); David Granville Stevenson, Bridge of Weir (GB)

(73) Assignee: VASCUTEK LIMITED, Renfrewshire, Strathclyde (GB)

( * ) Notice: Subject to any disclaimer, the term of this patent is extended or adjusted under 35 U.S.C. 154(b) by 19 days.

(21) Appl. No.: 14/123,675

(22) PCT Filed: Jun. 1, 2012

(86) PCT No.: PCT/GB2012/051248
§ 371 (c)(1),
(2), (4) Date: Jan. 8, 2014

(87) PCT Pub. No.: WO2012/164304
PCT Pub. Date: Dec. 6, 2012

(65) Prior Publication Data
US 2014/0114400 A1    Apr. 24, 2014

(30) Foreign Application Priority Data
Jun. 3, 2011    (GB) .................................. 1109315.0

(51) Int. Cl.
*A61F 2/848*    (2013.01)
*A61F 2/82*    (2013.01)
(Continued)

(52) U.S. Cl.
CPC ... *A61F 2/82* (2013.01); *A61F 2/07* (2013.01); *A61F 2/848* (2013.01); *A61F 2/89* (2013.01);
(Continued)

(58) Field of Classification Search
CPC ..................................... A61F 2/07; A61F 2/89

USPC ................................................. 623/1.13, 1.16
See application file for complete search history.

(56) References Cited

U.S. PATENT DOCUMENTS

| 4,580,568 A | 4/1986 | Gianturco |
| 5,720,776 A | 2/1998 | Chuter et al. |

(Continued)

FOREIGN PATENT DOCUMENTS

| EP | 0686379 | 12/1995 |
| EP | 0880949 A1 | 12/1998 |

(Continued)

OTHER PUBLICATIONS

Parodi et al., Annals of Vascular Surgery (1991) 5:491-499.
(Continued)

*Primary Examiner* — Thomas J Sweet
*Assistant Examiner* — Wade P Schutte
(74) *Attorney, Agent, or Firm* — Heslin Rothenberg Farley & Mesiti P.C.

(57) ABSTRACT

There is provided a device to secure a prosthesis, such as a stent graft, to the internal wall of a body lumen. The device is formed from two elongate elements each comprising a central portion with at least one arm extending therefrom. The central portions of the elements abut. Optionally, the central portions are joined together, optionally by a joining element which can act as a hinge. The terminal end of each arm can be shaped for engagement with the inner surface of the body lumen. The device is reversibly interchangeable between a first folded configuration and a second deployed or open configuration. The device is preferably attached to the sleeve of a stent graft independent of the stents which are preferably ring stents. A stent graft comprising the device is also described.

13 Claims, 6 Drawing Sheets

Figure 1:
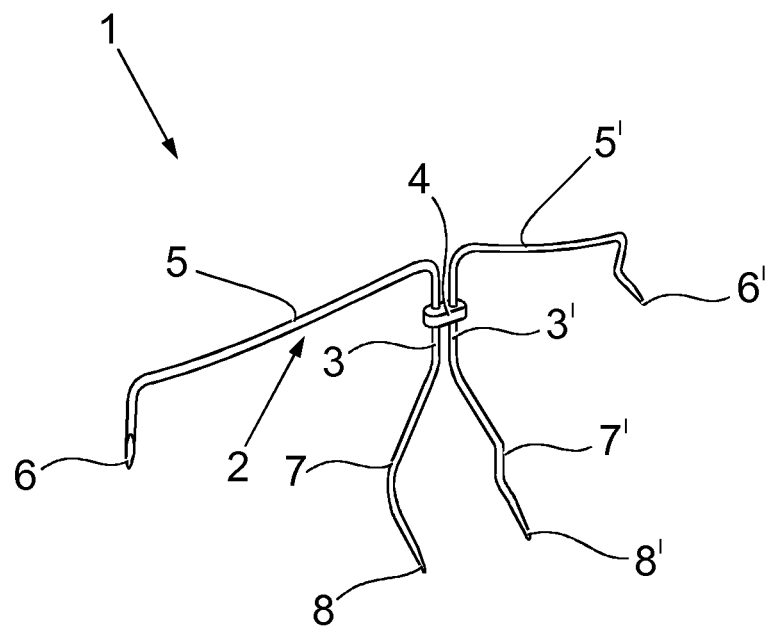

(51) Int. Cl.
*A61F 2/07* (2013.01)
*A61F 2/89* (2013.01)

(52) U.S. Cl.
CPC ... *A61F 2002/075* (2013.01); *A61F 2002/8483* (2013.01); *A61F 2220/0016* (2013.01); *A61F 2230/0095* (2013.01)

(56) References Cited

U.S. PATENT DOCUMENTS

| | | |
|---|---|---|
| 6,203,568 B1 | 3/2001 | Lombardi et al. |
| 6,231,581 B1 * | 5/2001 | Shank et al. ............. 606/157 |
| 6,278,079 B1 | 8/2001 | McIntyre et al. |
| 6,635,080 B1 | 10/2003 | Lauterjung et al. |
| 2002/0123790 A1 | 9/2002 | White et al. |
| 2005/0273155 A1 | 12/2005 | Bahler et al. |
| 2008/0114398 A1 | 5/2008 | Phillips et al. |

FOREIGN PATENT DOCUMENTS

| | | |
|---|---|---|
| EP | 1796589 | 8/2010 |
| WO | 8908433 A1 | 9/1989 |
| WO | 9607371 A1 | 3/1996 |
| WO | 9737617 | 10/1997 |
| WO | 9827894 A1 | 7/1998 |
| WO | 02085254 A1 | 10/2002 |
| WO | 2006034340 | 3/2006 |
| WO | 2010068589 A1 | 6/2010 |

OTHER PUBLICATIONS

United Kingdom Intellectual Property Office Search Report dated Sep. 27, 2012 for GB1209841.4.

International Search Report dated Sep. 25, 2012 for PCT/GB2012/051248.

Nienaber CA(1), Kische S, Ince H. "Thoracic aortic stent-graft devices: problems, failure modes, and applicability." Semin Vasc Surg. Jun. 2007;20(2):81-9. Division of Cardiology, University Hospital Rostock, Rostock School of Medicine, Rostock, Germany. christoph.nienaber@med.uni-rostock.de.

Ueda T(1), Fleischmann D, Dake MD, Rubin GD Sze DY. "Incomplete endograft apposition to the aortic arch:bird-beak configuration increases risk of endoleak formation after thoracic endovascular aortic repair." Radiology. May 2010;255 (2):645-52. doi: 10.1148/radiol.10091468. Department of Radiology, Stanford University School of Medicine.

Office Action for European Application No. 12731617.2 dated Mar. 24, 2016.

* cited by examiner

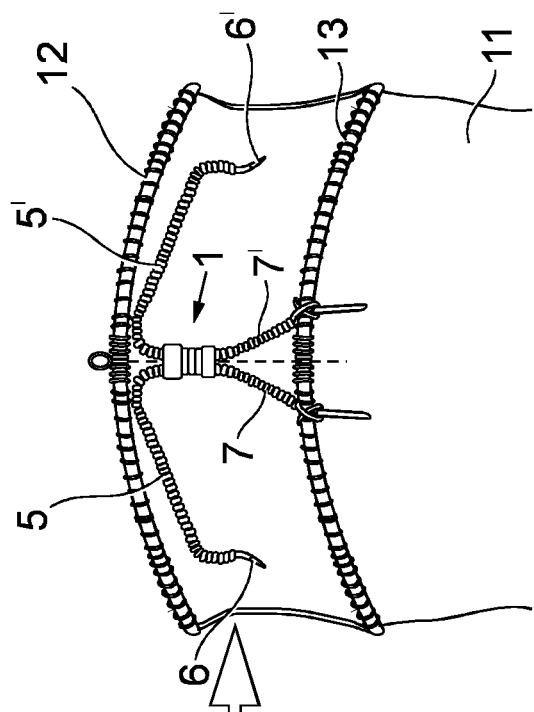
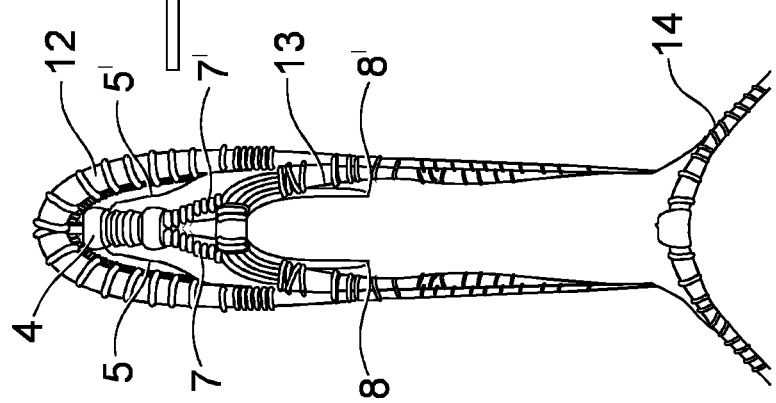

DEVICE FOR SECURING A PROSTHESIS TO THE INTERNAL WALL OF A BODY LUMEN

This application is a 371 of international application PCT/GB2012/052148, filed Jun. 1, 2012, and claims priority from GB application 1109315.0, filed Jun. 3, 2011, which is incorporated herein by reference in its entirety.

The present invention relates to a device for a tubular prosthesis, and in particular to a device to secure a tubular prosthesis to the internal wall of a body lumen into which it is placed.

Artificial prostheses consisting of a tubular conduit having an open lumen are well-known and are used in medicine to replace diseased or damaged natural body lumens, such as, for example, blood vessels or other hollow organs for example bile ducts, sections of intestine or the like. The most common use of such artificial prostheses is to replace diseased or damaged blood vessels.

A number of vascular disorders can be treated by use of an artificial prosthesis. One relatively common vascular disorder is an aneurysm. Aneurysm occurs when a section of natural blood vessel wall, typically of the aortic artery, dilates and balloons outwardly. Whilst small aneurysms cause little or no symptoms, larger aneurysms pose significant danger to a patient. Rupture of an aortic aneurysm can occur without warning and is usually fatal, so significant emphasis is placed on early diagnosis and treatment. With an increasingly ageing population, the incidence of aneurysm continues to rise in western societies.

Provided that an aneurysm is diagnosed prior to rupture, surgical treatment to repair the affected vessel wall is effective. Surgical treatment of aneurysm involves the replacement or reinforcement of the aneurismal section of aorta with a synthetic graft or prosthesis under general anaesthesia allowing the patient's abdomen or thorax to be opened (see Parodi et al., Annals of Vascular Surgery (1991) 5:491-499). The patient will then have a normal life expectancy.

Surgical repair of aneurysm is however a major and invasive undertaking and there has been much effort in developing less invasive methods. Currently, aneurysm repair generally involves the delivery by catheter of a fabric or ePTFE graft which is retained at the required location by deployment of metallic devices (stents). The ability to deliver the stent-graft device by catheter reduces the surgical intervention to a small cut-down to expose the femoral artery and, in suitable circumstances, the device can be deployed percutaneously. Catheter delivery is beneficial since the reduced invasive nature of the procedure allows utilisation of a local anaesthesic and leads to reduced mortality and morbidity, as well as decreased recovery time. For example, endovascular repair is typically used for repair of infra-renal abdominal aortic aneurysms where the graft is placed below the renal arteries. Many different types of devices useful for endovascular repair are now available, for example a resiliently engaging endovascular element described in U.S. Pat. No. 6,635,080 (Vascutek) or a tubular fabric liner having a radially expandable supporting frame and a radiopaque marker element stitched to the liner as disclosed in U.S. Pat. No. 6,203,568 (Medtronic).

However, whilst the endovascular repair of aneurysms is now accepted as the method of choice, the technique has significant limitations and is not suitable for all patients.

Endovascular techniques involve the delivery of the prosthesis by catheter. Since the internal lumen of the catheter defines the maximum dimensions of the prosthesis to be inserted, much effort has been expended in the design of prostheses which can be packaged in a minimal volume, and are easy to deploy once positioned at the required location.

One successful type of prosthesis consists of a stent graft comprising a conduit formed of a flexible sleeve attached to a rigid support or stent. The sleeve will typically be made of a fabric (usually a knitted or woven fabric) of ePTFE, PTFE, polyester (for example DACRON), polyethylene or polypropylene and may optionally be coated to reduce friction; discourage clotting or to deliver a pharmaceutical agent. The fabric will generally be porous on at least one surface to enable cell ingrowth. The stent may be balloon-expandable (eg. a PALMAZ stent made of rigid stainless steel wire), but could also be self-expandable and formed of a shape memory material, such as nitinol (a nickel-titanium alloy). Numerous different stent designs are known in the art (see for example braided stents described in EP 880949 or wire zig-zag stents described in U.S. Pat. No. 4,580,568).

The stent grafts are inserted using a delivery catheter and, once correctly located at the site requiring treatment, are deployed by the withdrawal of a delivery sheath of the delivery catheter. Balloon-expandable grafts are then caused to expand in diameter by inflation of a balloon located within the lumen of the graft. Self-expandable grafts radially expand upon release from the delivery sheath. Irrespective of the mode of expansion, once deployed, the stents hold the graft in location by contact with the inner wall of the blood vessel.

Since the stent will need to be compressed for loading into the catheter and during delivery, in general terms, the stent is formed from the minimum amount of material able to maintain the patency of the sleeve lumen at the required diameter.

However, it is often difficult for the surgeon to ensure that the stent graft is incorporated securely and held firmly in place in the lumen of the vessel within which it has been placed, since movement of the vessel and the pressure of blood flow may cause movement or migration of the stent graft in the direction of blood flow. This can be particularly problematic when the graft is used within major vessels such as the aorta and aortic arch, since blood flow in this region is at high pressure can exert high forces on an implanted graft.

Migration of stent grafts with a blood vessel is known to lead to numerous problems for the patient and increases the potential for stent graft failure.

There exists the need for safe and efficient means to secure a prosthesis, such as a vascular graft, particularly a stent graft, to the internal surface of the body lumen into which the prosthesis is located. The securement means must not, however, compromise packaging of the graft for endovascular delivery and must also avoid premature engagement (to the delivery sheath or body lumen) prior to correct placement of the graft.

The present invention provides a device for securing a prosthesis to the internal wall of a body lumen, such as a blood vessel. In particular the device of the present invention is suitable for endovascular delivery attached to the prosthesis.

In one aspect, the present invention provides a device comprising two elongate elements, each elongate element comprising a central portion with at least one arm extending at an angle therefrom, wherein the central portions abut, that is the central portions lie side-by-side and are longitudinally aligned. Optionally, the central portions are joined together at a joint. Optionally the central portions are joined by a joining element which holds the central portions together. In one embodiment, the joining element can act as a hinge such that the elongate elements are rotatable about the hinge. A suitable material for the joining element is tantalum since this has a high degree of corrosion resistance. Alternatively the central portions can be joined by thread, (ie. can be sewn together or joined by winding thread around the central portion and fastening the thread end), with the thread holding the two elongate elements in abutment together at the central portion. Optionally the thread sews the elongate elements onto a fabric graft. The thread can act as a hinge. Suitable biocompatible thread is known in the art. Materials that can be used as non-absorbable sutures are appropriate. Suitable materials include silk, nylon, polyester, polypropylene or polyethylene, for example ultra high molecular weight polyethylene. The thread could be in braided form. A further alternative is that the central portions are formed integrally from a single piece of material, for example by laser etching from a single piece of material. Alternatively, the central portions can be joined by laser welding.

The arm of each elongate element preferably extends outwardly from the central portion.

The terminal end of each arm (i.e. distal to the central portion) can be shaped for engagement with the inner surface of a body lumen. Thus the terminal end of the arm could be pointed, hooked, barbed or be in any other suitable configuration to engage with the inner surface of a body lumen.

The elongate elements can have a kink or curve prior to the terminal ends.

The elongate elements of the device are each independently resiliently deformable such that the angle formed between arms of the elongate elements can be reduced for packaging and/or for delivery of the prosthesis, but can be increased following deployment of the prosthesis on its release from the delivery sheath of the catheter. Increasing the angle between the arms causes the terminal ends to be spaced more widely from each other. Spacing the terminal ends from each other means that the device is attached to the inner surface of the body lumen at two separate locations which provides a more stable attachment.

The device of the present invention is reversibly interchangeable between a first configuration and a second configuration.

In the first configuration, suitable for packaging of the prosthesis in a catheter and for its delivery by endovascular techniques, the outwardly extending arms of the device are urged inwardly and/or rotated about a hinge element so that the angle formed between the arms is decreased and the terminal ends approach each other. In one embodiment the first configuration is adopted due to the application of external pressure, such as a close fitting sleeve being placed externally over the stent graft. In this first configuration, since the terminal ends are held close together, the deployment of the device from an external sleeve is less likely to be adversely affected by the terminal ends becoming snared on the internal surface of the sleeve or attaching prematurely to the inner surface of the body lumen prior to full deployment of the prosthesis.

In the second configuration, adopted once the external pressure caused by packaging of the device is removed, the arms spring resiliently outwardly adopting a more open configuration with a wider angle between the arms and thus increasing the spacing between the terminal ends. Simultaneously, the central portions can rotate within a hinge element (if present) to urge the arms outwardly and the terminal ends apart.

The device will be positioned on the external face of the prosthesis so that the terminal ends are presented for enagagement with the inner surface of the body lumen into which the prosthesis is located.

The central portions can be independently configured for attachment to the prosthesis, conveniently by attachment to a fabric sleeve thereof. For example the central portion can include an eye or aperture which can be attached to the sleeve of a stent graft, for example by sewing. Alternatively any joining or hinge element can include external projections at its upper and lower edges so that stitches placed around its circumference cannot slip off. Other attachment means are also possible, for example heat bonding, use of adhesive and the like.

Conveniently, at least one arm of each elongate element (ie. the end of each arm not attached to the central portion) can be configured for independent attachment to the prosthesis, for example by attachment to a fabric sleeve thereof. For example, the or each arm configured for attachment can include an eye or aperture which can be attached to the sleeve of a stent graft, for example by sewing. Other attachment means are also possible, for example heat bonding, use of adhesive and the like.

Each elongate element can be formed of any suitable biocompatible material having the necessary resilience to fold inwardly into a first folded configuration (ie. for packaging) and to adapt a second open configuration (ie. after deployment). Mention can be made of shape memory materials such as, for example, nitinol. Resilient polymers are also suitable, particularly engineering high modulus polymers such as polyether ether ketone (PEEK). PEEK polymers with shape memory behaviour can be used.

The elongate elements of the device of the present invention can conveniently be formed by laser cutting, for example, by laser cutting from a planar sheet or cylindrical tube of material. This method allows a suitable degree of accuracy in forming the elongate elements. Generally the planar sheet of material (for example nitinol) will be of 0.1 mm to 1.0 mm thickness, preferably from 0.2 mm to 0.9 mm, but other thicknesses including 0.3, 0.4, 0.5, 0.6, 0.7, 0.8 mm are also possible. In one embodiment both elongate elements are formed integrally with the joint between the central portions by laser etching from a single piece of material, such as a nitinol sheet. In an alternative embodiment each elongate element is formed by laser etching from nitinol sheet and are then placed in abutment or joined to each other, for example by stitching or winding thread around the central portions, preferably so that the two elongate elements can rotate relative to each other.

In one embodiment, each elongate element has a central portion and a single resilient arm extending outwardly from the central portion. The two elongate elements are joined together at a joint, which can include an external joining element, such as a tantalum join or thread. In this embodiment, the device can adopt a "V"-shape configuration following deployment. Each elongate element can conveniently be formed from nitinol, for example can be laser etched from a nitinol sheet, and optionally both are laser etched from a single piece of nitinol.

The device of the invention can comprise two elongate elements, wherein each elongate element has a central portion with two arms extending outwardly from the central portion above and below the central portion. The two central portions are joined together as indicated above. Thus, the device comprises four arms in total, and adopts an "X"-shaped configuration following deployment. Where the elongate elements are formed as separate items, they can be placed in abutment or joined together at their central portions by a joining element eg. thread or a tantalum joint. Optionally the upper arms of each of the elongate elements have a first angle relative to each respective central portion, and the lower arms have a second angle relative to the respective central portion. In this embodiment, where the device has four arms, attachment of each of the arms to the prosthesis may be sufficient for attachment to the device and it is not necessary to also attach the central portions to the sleeve, although this additional attachment remains an option. Alternatively, the central portions and the upper arms can be attached to the prosthesis.

Where each elongate element comprises two arms, located above and below the central portion, the device can be symmetrical about the longitudinal axis between the central portions, that is the elongate elements can be mirror images of each other.

The arms can have an arcuate profile. Thus, in this embodiment, the arms are curved rather than straight. This enables the arms to extend at least partially around the circumference of a tubular prosthesis (such as a vascular graft) to which the device is attached. Thus, the arms can conform to the circular cross-section of the prosthesis to which they are attached, ensuring a close fit.

The device is particularly suitable for use with a stent graft, particularly of the type used to treat aneurysm. In one embodiment, the device of the present invention is used in combination with a stent graft comprising a fabric sleeve with a number of ring stents attached to the sleeve. The device of the present invention can be located between any two neighbouring ring stents on such a stent graft.

The device can be located between two neighbouring ring stents and attached to the sleeve of the stent graft at or close to the location of each of the two neighbouring ring stents. Conveniently, the device is attached to the sleeve by sewing, but any other suitable means of attachment to the sleeve (eg. adhesive or heat bonding) could alternatively be used. Attachment to the sleeve (as opposed to the ring stents) reduces the potential for fracture of the stent and subsequent mechanical weakness.

Two arms of the device can be attached to the sleeve at or adjacent (for example immediately adjacent) to a first ring stent independently attached to the sleeve, and a different portion of the device (such as the joint (including a joining or hinge element) or two other arms) of the device is attached to the sleeve at a different location, for example in the portion of the sleeve between the first ring stent and a second ring stent which is its immediate neighbour or adjacent (for example immediately adjacent) to the second ring stent independently attached to the sleeve.

The device of the present invention can comprise two elongate elements, joined as described above, each elongate element having upper and lower arms extending outwardly from a central portion located between the upper and lower arms, wherein the upper arm of each elongate element is attached to the sleeve at or adjacent (for example immediately adjacent) to a first ring stent independently attached to the sleeve, and each lower arm of the elongate element is attached to the sleeve at or adjacent (for example immediately adjacent) to a second ring stent independently attached to the sleeve. Optionally the lower arms of each elongate element cross the second ring stent (i.e. run under or over the ring stent) and are attached to it at this junction.

Conveniently, the device is located between a terminal ring stent and its immediate neighbour. This position has the advantage of increasing column stiffness at the end of the prosthesis, thereby increasing patency and improving the seal between the outer wall of the prosthesis and the inner surface of the natural blood vessel into which it has been located.

In one aspect, the present invention provides a stent graft comprising:
i) a sleeve having a first end and a second end with a lumen extending therethrough;
ii) at least two ring stents attached to the sleeve a pre-selected distance apart; and
iii) two elongate elements which abut at a central portion thereof, each central portion having at least one arm extending outwardly therefrom, wherein the elongate elements are attached to the sleeve and bridge the distance between the ring stents.

The central portion of the two elongate elements can be joined together by a joining element which preferably acts as a hinge. A suitable hinge joining element is thread, where the elongate elements are attached by stitches or by winding the thread and fastening the ends. The stitches used to join the central portions of the two elongate elements can also attach the central portions to the sleeve. In one embodiment each elongate element can be independently sewn onto the sleeve so that the central portions are adjacent (side-by-side) and are aligned. Optionally, the two central portions can then be over sewn together, using joining stitches which encompass both central portions, so that the joining stitches act as a hinge. Braided polyester thread can be used for sewing the central portions together, though other threads are also suitable.

The graft sleeve can be flexible and is usually formed of a woven or knitted fabric. The sleeve will usually be substantially impervious to fluid. Optionally, at least one surface of the sleeve will be sufficiently porous to facilitate cell ingrowth. Suitable materials include polyester, polyethylene, polypropylene, ePTFE, PTFE and the like. The sleeve can be coated to reduce permeability or to deliver a biological agent.

For many intended purposes, the sleeve can conveniently be formed with a constant diameter. However tapered grafts (ie. where the diameter varies along its length) are also possible and are particularly useful for certain indications.

In a further aspect, the present invention provides an implantable prosthesis comprising:
i) a compliant and substantially fluid impervious tubular sleeve having a proximal end and a distal end with a conduit therethrough;
ii) a first ring stent formed from multiple windings of wire of a shape memory material, attached to said sleeve at a first location;
iii) a second ring stent formed from multiple windings of wire of a shape memory material, attached to said sleeve at a second location; and
iv) two elongate elements, each elongate element having a central portion with at least one arm extending outwardly therefrom, wherein the central portions abut;
wherein a first portion of each elongate element is attached to said sleeve at said first location, and wherein a second portion of each elongate element is attached to said sleeve at said second location.

The central portions of the two elongate elements can be joined together by a joining element, for example a tantalum crimp or thread (for example braided polyester). Optionally the joining element acts as a hinge such that the arms are rotatable. A suitable hinge joining element is thread, where the elongate elements are attached by stitches or by winding the thread and fastening the ends. The stitches used to join the central portions of the two elongate elements can also attach the central portions to the sleeve. In one embodiment each elongate element can be independently sewn onto the sleeve so that the central portions are adjacent (side-by-side) and are aligned. Optionally, the two central portions can then be over sewn together, using joining stitches which encompass both central portions, so that the joining stitches act as a hinge.

The ring stents can each be formed from nitinol wire and will typically include multiple windings of nitinol wire. Each ring stent can be attached to the external surface of the sleeve or to the internal (luminal) surface of the sleeve. Generally, it is more convenient to attach the ring stents to the external (non-luminal) surface of the sleeve.

In an embodiment of the stent graft of the present invention, one of said ring stents is located at or close to the first or second ends of the sleeve. For example, although distances will vary with dimensions of the stent graft, one ring can conveniently be located from 0 to 2 cm from either the first or second end of the sleeve.

A suitable pre-selected distance for the closest point between the two ring stents is from 0.1 to 8 cm, preferably 0.5 to 5 cm, more preferably between 0.5 to 3 cm. One of skill in the art will however be aware that the pre-selected distance between the ring stents will depend upon factors such as the size (diameter and/or length) of the stent graft, its intended location in the patient, the patient's anatomy and medical condition.

The two ring stents can conveniently be immediate neighbours (ie. there will be no other ring stents attached to the sleeve in the space between them).

In the stent graft of the present invention, one portion of each elongate element will be attached to the sleeve at or adjacent (for example immediately adjacent) to the location of one ring stent, and another portion of each elongate element will be attached to the sleeve at or adjacent (for example immediately adjacent) to the other ring element. For example, one arm of each elongate element can be attached to the sleeve at or adjacent to the first ring element and either the central portions or a second arm of each elongate element can be attached to the sleeve at or adjacent to the second ring element.

In one embodiment, the two elongate elements are each formed from nitinol, preferably from heat set nitinol wire.

The stent graft can comprise a ring stent formed by multiple windings of resilient wire, for example nitinol wire. Optionally each ring stent can be formed from a plurality of strands of wire, but other designs of ring stents are also possible. The number of strands of wire can be varied according to the wire utilised and the size of graft. The number of strands wound can vary from 2 to 120 or even more, but would typically have 10 to 30 strands forming the ring stent. Any diameter wire which maintains the required resilience can be used. Suitable diameters can be selected from a range of 0.1 mm to 2 mm, for example 0.5 mm to 1 mm.

Conveniently each ring stent is attached to the sleeve by suitable attachment means, for example by mechanical means (such as sewing), by chemical means (such as adhesive) or by thermal means (for example heat bonding).

It is possible for the stent graft of the invention to include multiple ring stents, and the stent graft of the invention is not limited to any particular number of ring stents.

For some embodiments the stent graft can have for example 3 to 15 ring stents but other numbers of ring stents are also possible depending on the graft length and diameter.

Optionally at least one ring stent of stent graft adopts a saddle shape in its open (deployed) configuration. A ring stent will be saddle shaped if the circumference of the ring stent is larger than the circumference of the outer surface of the sleeve of the stent graft and the ring stent is attached in a sinusoidal (saddle-shaped) configuration, having two peaks and troughs. A saddle-shape can be beneficial in improving flexibility of the stent graft. Optionally the device is located between two ring stents, one or both of which are saddle-shaped. Optionally the device is located between two ring stents, one of which is a terminal ring stent of the stent graft, this terminal ring stent being saddle-shaped.

In one embodiment the stent graft of the invention includes a single device formed from two elongate elements as described above. Alternatively the stent graft of the invention includes 2 or more such devices. Where multiple devices are present, two devices can be located between the same two neighbouring ring stents, but diametrically opposite each other on the sleeve circumference.

Optionally the stent graft of the present invention includes devices located between ring stents at each end of the stent graft. Thus in this embodiment, at least one device is located between the terminal ring stent and its immediate neighbour at the first end of the sleeve and at least one device is located between the terminal ring stent and its immediate neighbour at the second end of the sleeve. In another embodiment at least one device may be located by protruding past the terminal ring at one end.

In a further aspect, the present invention provides a method of repairing a diseased vessel, said method comprising inserting a prosthesis into the vessel, said prosthesis comprising a flexible tubular conduit having at least two ring stents attached to the conduit at preselected locations thereon, and having two elongate elements as described above attached to each location. The prosthesis can be an implantable prosthesis or a stent graft as described above.

The present invention further provides a method of treating a body lumen, said method comprising inserting a stent graft into said lumen, said stent graft comprising:
i) a sleeve having a first end and a second end with a lumen extending therethrough;
ii) at least two ring stents attached to the sleeve a pre-selected distance apart; and
iii) two elongate elements, each elongate element having a central portion with at least one arm extending outwardly therefrom, wherein the central portions abut;
wherein a first portion of each said elongate element is attached to said sleeve at said first location, and wherein a second portion of each said elongate element is attached to said sleeve at said second location.

In a further aspect, the present invention provides a method of treating a patient in need thereof, said method comprising implanting a prosthesis comprising:
i) a compliant and substantially fluid impervious tubular sleeve having a proximal end and a distal end with a conduit therethrough;
ii) a first ring stent formed from multiple windings of wire of a shape memory material, attached to said sleeve at a first location;
iii) a second ring stent formed from multiple windings of wire of a shape memory material, attached to said sleeve at a second location; and
iv) two elongate elements joined together by a joining element or formed integrally in a single piece, each elongate element having central portion with at least one arm extending outwardly therefrom, wherein each elongate element is attached to the sleeve so that it bridges the distance between the ring stents.

The central portion of the two elongate elements can be joined together by a joining element, for example a tantalum crimp or thread (for example polyester braid). Optionally the joining element acts as a hinge so that the arms are rotatable. A suitable hinge joining element is thread, where the elongate elements are attached by stitches or by winding the thread and fastening the ends. The stitches used to join the central portions of the two elongate elements can also attach the central portions to the sleeve. In one embodiment each elongate element can be independently sewn onto the sleeve so that the central portions are adjacent (side-by-side) and are aligned. Optionally, the two central portions can then be over sewn together, using joining stitches which encompass both central portions, the joining stitches acting as a hinge.

In a further aspect, the present invention provides a method of manufacturing a prosthesis suitable for implantation into the body, said method comprising:
(i) providing a flexible tubular conduit;
(ii) providing two elongate elements each having central portion with first and second arms extending outwardly therefrom;
(iii) attaching said elongate elements to said conduit so that the central portions are aligned and adjacent;
(iv) attaching a first ring stent to the conduit; and
(v) attaching a second ring stent to said conduit.

Said first ring stent can be at or adjacent said first arms and said second ring stent can be at or adjacent said second arms. In other words the elongate elements bridge the gap between the first and second ring stents.

The central portion of the two elongate elements can be joined together by a joining element which for example a tantalum crimp or thread (for example polyester braid). Optionally the joining element acts as a hinge so that the arms are rotatable. A tantalum crimp can be used as the joining element and attached to the elongate elements to form an integral device prior to attachment of the device to the sleeve. An alternative hinge joining element is thread, where the elongate elements are attached by stitches or by winding the thread and fastening the ends. The stitches used to join the central portions of the two elongate elements can also attach the central portions to the sleeve. In one embodiment each elongate element can be independently sewn onto the sleeve so that the central portions are adjacent (side-by-side) and are aligned. Optionally, the two central portions can then be over sewn together, using joining stitches which encompass both central portions, the joining stitches acting as a hinge.

In an alternative embodiment the two elongate elements can be formed integrally as a single piece.

The elongate elements can be attached to the exterior surface of said conduit. In this embodiment the first and second ring stents are also preferably attached to the exterior surface of said conduit. One ring stent can overlie at least a portion of the elongate element. Alternatively the elongate elements can cross over one or both of the ring stents. Depending upon the configuration required, step (iii) can be performed prior to or after steps (iv) and (v). Thus, the order of steps (iii) to (v) can be varied depending upon the final configuration required and convenience of manufacture. Whilst any means of attachment can be used to secure the elongate elements and the ring stents to the conduit, conveniently the elongate elements are attached by sewing, preferably by stitches located about each arm. Optionally, each of the ring stents is also attached by sewing.

In one embodiment, one elongate element is located so that its central portion is positioned to be between the ring stent positions and attached to the conduit by stitching, the stitches lying over the central portion and passing through the wall of the conduit at either side of the elongate element. Braided polyester thread can be used, although other thread types are also possible. The second elongate element is then aligned so that is central portion abuts the central portion of the first elongate element. The second elongate element is then attached to the conduit by stitching, the stitches lying over the central portion and passing through the wall of the conduit at either side of the elongate element. The central portions of the two elongate elements are then oversewn, each over sewing stitch passing through the wall of the conduit next to one elongate element, over both elongate elements and through the wall of the conduit next to the other elongate element. Braided polyester thread can be used, although other thread types are also possible. It should be noted that the upper and lower arms of each elongate element can also be attached by stitching, as required. The ring stents are then attached to the conduit (in any convenient order). The terminal ring stent will usually lie adjacent to a portion of the upper arms of the elongate elements, whilst the non-terminal ring stent will cross over the lower arms. A portion of the lower arms of each of the two elongate elements will thus lie beneath the non-terminal ring stent.

Preferred or alternative features of each aspect or embodiment of the invention apply mutatis mutandis to each other aspect or embodiment of the invention, unless the context demands otherwise.

Figure 2:
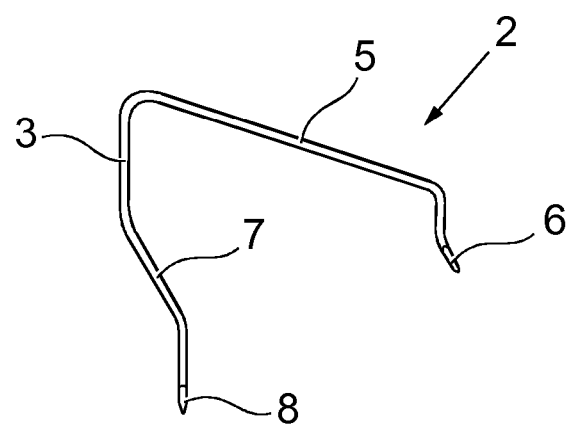
Figure 3:
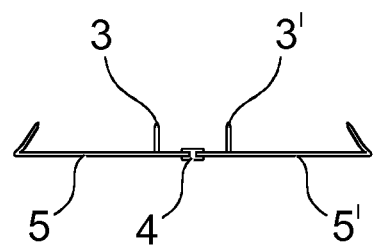
Figure 4:
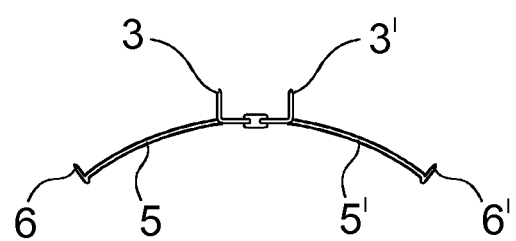
Figure 5:
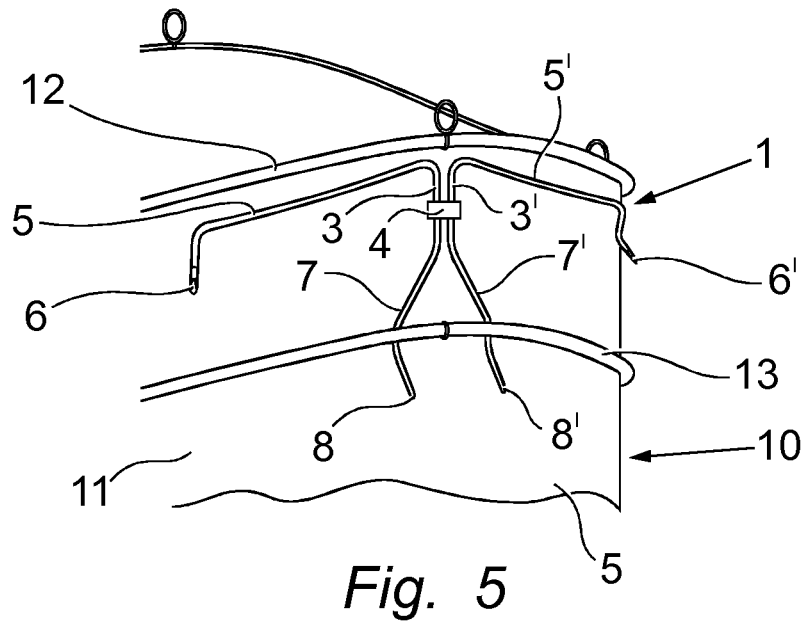
Figure 6:
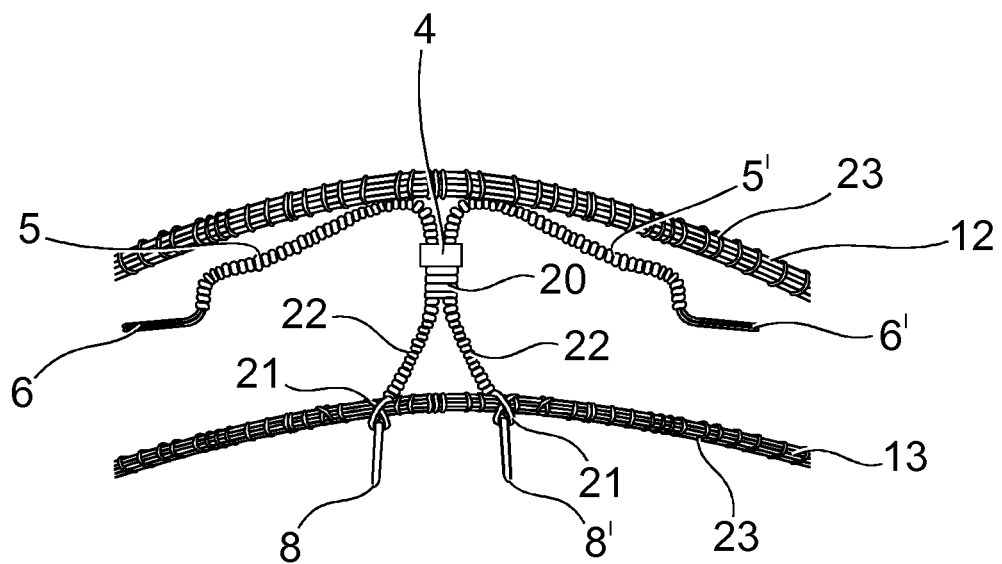
Figure 9:
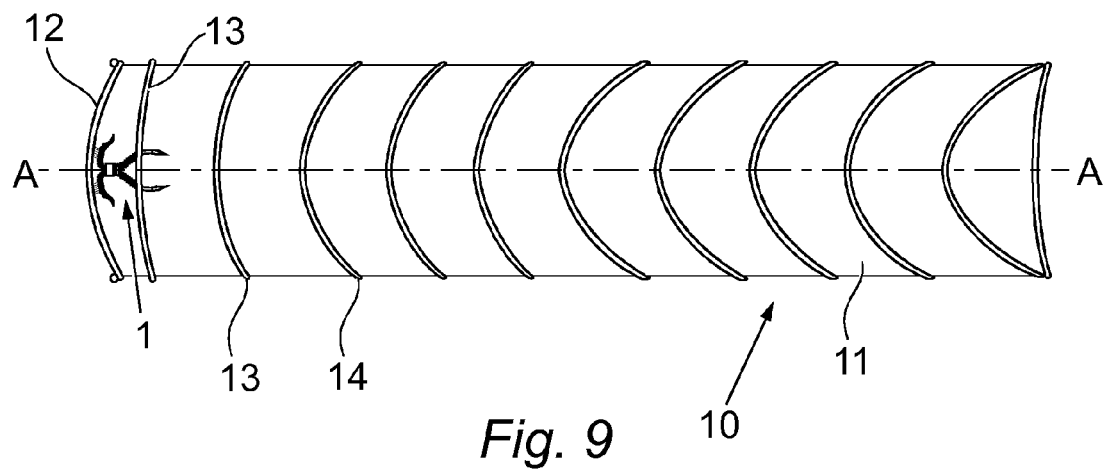
Figure 10:
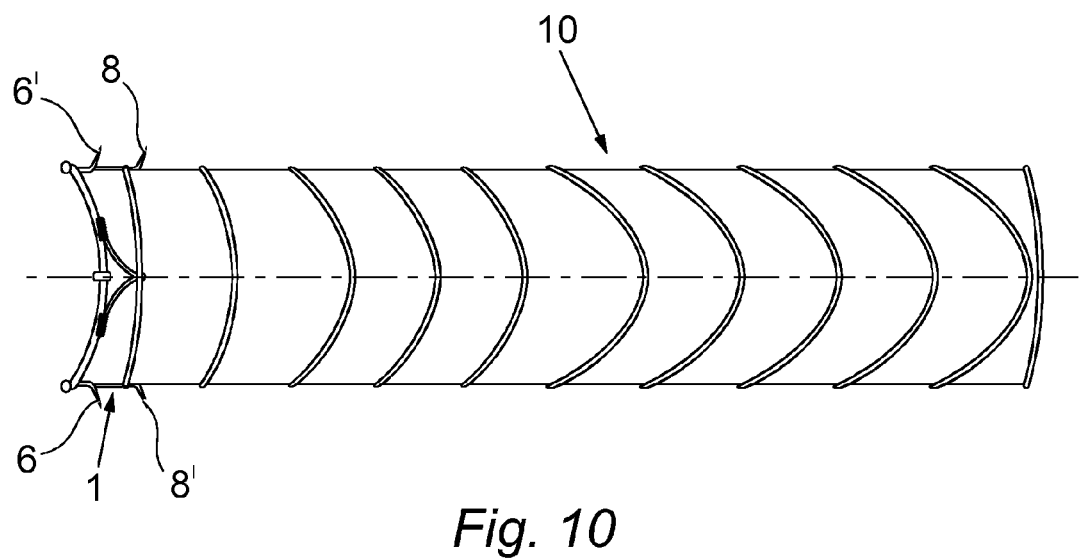

The present invention will now be further described by reference to the following figures, in which:

FIG. 1: is a schematic illustration of one embodiment of the device of the invention comprising two elongate elements in open (deployed) configuration;

FIG. 2: is a schematic illustration of one elongate element of the device of FIG. 1;

FIG. 3: shows the top view of a device of the present invention at an intermediate stage in its manufacture;

FIG. 4: shows the bottom view of the device of FIG. 3 after it has been heat set to be in arcuate form;

FIG. 5: shows the device of FIG. 1 attached to one end of a tubular prosthesis which includes two ring stents;

FIG. 6: shows detail of the attachment of the device and ring stents of FIG. 5;

FIG. 7: shows the device of FIG. 1 with the prosthesis in compacted form for delivery;

FIG. 8: shows the device of FIG. 1 with the prosthesis in expanded form following delivery;

FIG. 9: shows a deployed stent graft prosthesis which comprises two devices of FIG. 1 (only one device is shown);

FIG. 10: shows the side view of the prosthesis of FIG. 9; and

Figure 11:
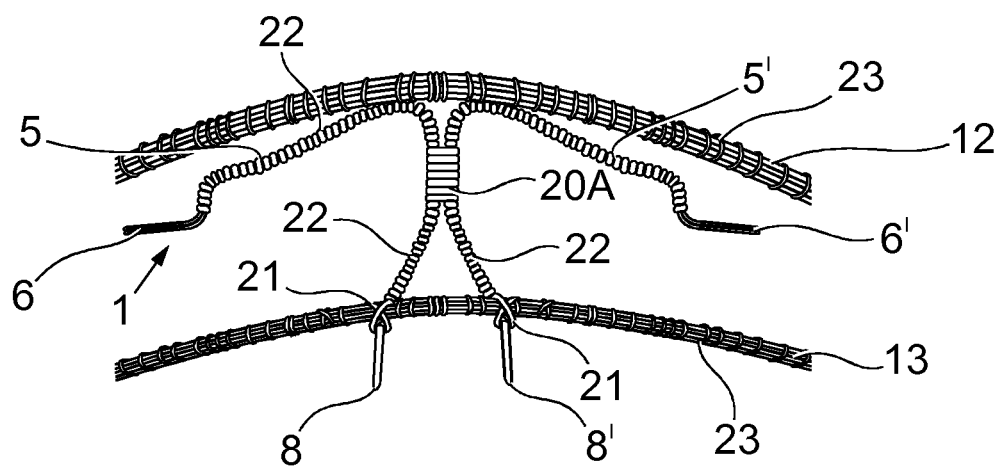

FIG. 11: shows a device of the present invention attached to a tubular prosthesis.

Referring to the drawings, FIG. 1 shows a device (1) of the invention formed from nitinol and having two elongate elements (2) each with a central portion (3, 3'). The central portions (3, 3') are joined at joining element (4) which can conveniently be formed from tantalum. The tantalum joining element shown can be replaced by using thread wound around central portions (3, 3') and the ends fastened or by stitches. In the embodiment illustrated the joining element (4) can act as a hinge so that the elongate elements can rotate, but it is also possible to have the device formed from a single piece of material, so that the joining element will be a bridge between the central portions (3, 3') or the device can be formed with a single central portion. In the embodiment illustrated, each elongate element (2) has an outwardly extending upper arm (5, 5') with a terminal end (6, 6'). Each elongate element (2) also has an outwardly extending lower arm (7, 7') with a terminal end (8, 8'). The terminal ends (6, 6', 8, 8') are each shaped to project radially outwardly and have a pointed end or hook for engagement with the inner wall of a body lumen following deployment. As illustrated in FIG. 1, the device (1) is shown in an open configuration in which the upper and lower pairs of arms (5, 5', 7, 7') have adopted a wide angle with the terminal ends (6, 6', 8, 8') spaced apart from each other.

FIG. 2 shows an elongate element (2) in more detail. Elongate element (2) is conveniently produced by conforming nitinol wire of diameter 0.53 mm on a steel tool and heat setting, for example at a temperature of 550° C. for 6 minutes. The elongate element (2) is then electropolished in order to increase fatigue life and to ensure an accurate final crosssectional size. Two of the elongate elements as shown in FIG. 2 can be placed in abutment. Optionally the elongate elements can be joined together by a joining element (4) (for example by stitches across the central portion (4) onto the fabric sleeve of a prosthesis) and optionally configured such that central portion (3) can rotate about its longitudinal axis.

FIG. 3 shows a top view of the device as shown in FIG. 1 at an intermediate stage of its manufacture. As illustrated, the upper arms (5, 5') extend in a straight line from central portion (3) and joining element (4). The joining element shown is a tantalum crimp, but alternatively should be stitches or wound thread. Attachment to a tubular prosthesis could cause deformation in the prosthesis shape. Accordingly, it is preferred that the device is heat set or otherwise permanently formed in an arcuate shape.

FIG. 4 shows a bottom view of the device formed into a suitable arcuate shape. The upper arms (5, 5') extend in a curved line from the central portion (3) and joining element (4). Advantageously, the arc described by the arms of device (1) has a circumference which matches the outer circumference of the tubular prosthesis to which the device is to be attached. This ensures a snug fit between the device and the outer surface of the prosthesis.

In FIG. 5, the device (1) of FIG. 1 is shown in position on the exterior of a stent graft (10). Stent graft (10) is formed from a flexible tubular conduit or sleeve (11) having a number of ring stents (12, 13) attached thereto to maintain the patency of the sleeve lumen after deployment. The ring stents (12, 13) can conveniently be formed from multiple windings of nitinol wire. Only one end portion of stent graft (10) is illustrated, for convenience. In the end portion of stent graft (10) illustrated in FIG. 5, the stent graft (10) terminates with a first ring stent (12) which is spaced a pre-determined distance apart from its neighbouring ring stent, second ring stent (13). The device (1) is shown attached between the first and second ring stents (12, 13). The upper arms (5, 5') of device (1) are shown located just below the first ring stent (12). Terminal ends (6, 6') of upper arms (5, 5') project outwardly from the exterior surface of sleeve (11), as best seen with end 6', in order to engage with the inner surface of a body lumen after placement of the stent graft (10), thereby holding the stent graft (10) firmly in place. The lower arms (7, 7') of device (1) are shown located crossing underneath second ring stent (13). Thus, device (1) is attached to the fabric sleeve (11) before attachment of the second ring stent (13). Alternatively device (1) could cross over ring stent (13), and be attached to the sleeve (11) after ring stent (13). Terminal ends (8, 8') of lower arms (7, 7') project outwardly from the exterior surface of sleeve (11), in order to engage with the inner surface of a body lumen thereby holding the stent graft (10) firmly in place. The joining element (4) can be formed from stitches (for example using braided polyester) across both central portions (3, 3') which act to hold the elongate elements together and locate them on the fabric sleeve (11).

Fabric sleeve (11) is a woven or knitted flexible fabric which is generally impervious to fluid such as blood. Suitable materials include polyester, such as Dacron. Fabric sleeve (11) may optionally be coated to reduce blood clotting, to reduce friction or to deliver a medicament. The stent graft (10) shown in FIG. 5 is depicted in the expanded (deployed) configuration.

FIG. 6 shows detail of the attachment of ring stents (12, 13) to sleeve (11) in the stent graft (10) of FIG. 5 and also shows detail of the attachment of device (1) to the sleeve (11). As illustrated, the central portion (3, 3') of device (1) has been attached using stitches (20). Other forms of attachment are also possible. Additionally, the location of arms (7, 7') beneath second ring stent (13) occurs prior to the stitching of second ring stent (13) onto sleeve (11), though as mentioned above, this configuration could be reversed with ring stent (13) being located below arms (7, 7'). Additional stitches (shown as cross-stitch) (21) are located about the junction where lower arms (7, 7') cross underneath second ring stent (13). Thus stitches (21) hold both lower arms (7, 7') and also ring stent (13) securely together on sleeve (11). Additional stitches (22) are located along the length of upper arms (5, 5') and lower arms (7, 7') of the device until the terminal ends thereof. As illustrated terminal ends (6, 6', 8, 8') are free from stitches in order to engage with the inner luminal wall of a body vessel. As illustrated in FIG. 6, arms (5, 5') are shaped to have a kink or bend immediately prior to the terminal ends (6, 6') which prevents the arms slipping within the stitches and presents the terminal ends (6, 6') outwardly when the device (1) is in its deployed mode. Also as illustrated in FIG. 6, lower arms (7, 7') are shaped to have a kink or bend immediately prior to the terminal ends (8, 8') which prevents the arms slipping within the stitches and presents the terminal ends (8, 8') outwardly when the device (1) is in its deployed mode. Stitches (23) hold first ring stent (12) and, separately, second ring stent (13) securely onto the outer surface of sleeve (11). Stitches (20, 21, 22, 23) may be formed by any convenient means, including hand stitching. Hand stitching has the advantage of accurate stitch placement. Advantageously suture material is used to sew the device (1) and/or ring stents (12, 13) onto sleeve (11). Braided polyester is suitable but other thread types can also be used. FIG. 6 shows first ring stent (12) and second ring stent (13) formed from multiple strands, for example of nitinol wire.

FIG. 7 shows a portion of the stent graft (10) of the invention in a folded configuration, suitable for insertion into a catheter and deployment into the body lumen of a patient, such as a blood vessel. In this configuration ring stents (12, 13) and any other ring stents of graft (10) are compressed and will be held in that compressed form by an outer delivery sheath which forms part of the delivery catheter (not shown). As illustrated, upper arms (5, 5') of device (1) are bent by compression of ring stent (12), such that the terminal ends (6, 6') approach each other and the angle between these ends is decreased. Similarly, the folding of ring stent (13) into its compressed form causes lower arms (7, 7') to be urged together such that the terminal ends (8, 8') are also brought close to each other and the angles between ends (8, 8') is decreased. Device (1) is formed of a resilient material, such as nitinol, which can tolerate such compression. Multiple windings of nitinol wire can be used to form each of the ring stents (e.g. ring stents 12, 13). A third ring stent (14) is also shown.

When the device is in its folded configuration, terminal ends (6, 6', 8, 8') are positioned closer to the proximal seal line of the graft and do not project outwardly. Thus, the possibility of premature attachment or snagging on the delivery sheath, delivery catheter or body lumen prior to full deployment is significantly reduced. FIG. 8 illustrates the stent graft (10) of FIG. 7 when deployed. Upon deployment of the stent graft (10) (for example by removal of the delivery sheath located around the compressed stent graft) upper arms (5, 5') spring outwardly, together with ring stent (12) which adopts its open, annular configuration. Likewise, lower arms (7, 7') also spring outwardly together with second ring stent (13) which adopts its open annular configuration. FIGS. 7 and 8 clearly show ring stents (12, 13) and device (1) attached to the sleeve (11) by stitches. Alternative forms of attachments are also possible. The joining element illustrated could be replaced by stitches across the central portions of the elongate elements.

As shown in FIG. 9, device (1) is as illustrated in FIG. 1 and is shown in its deployed configuration. Stent graft (10) comprises a flexible sleeve, for example formed of woven polyester such as Dacron. As illustrated, stent graft (10) comprises twelve separate ring stents, each spaced a predetermined distance apart. Alternative numbers or placements of stents are possible. The upper part of device (1) is attached to sleeve (11) at or adjacent to the location of first ring stent (12), with the lower arms (7, 7') passing underneath or above second ring stent (13). Third ring stent (14) is also labelled. Each ring stent is attached to the outer surface of sleeve (11). Device (1) is shown in its open (deployed) configuration and has a large angle between upper resilient arms (5, 5') and lower resilient arms (7, 7'). In its compressed configuration (not shown) the tips of arms (5, 5', 7, 7') will be urged together, for example by applying external pressure, such that the angle between each pair of arms (5, 5' and 7, 7') is decreased. Suitably, device (1) is attached to sleeve (4) by sewing using suture material. Conveniently, the ring stents can also be secured by sewing. Alternative forms of device 1 can be used with the stent graft (10) illustrated.

As illustrated in FIG. 9, the terminal ring stent (12) has a saddle shape with a trough approximately aligned with the central portion (4) of device (1) on the longitudinal axis A-A. As illustrated, second ring stent (13) is of a more annular configuration, and the ring stents in the central position of the prosthesis have an increased saddle shape, which can be independently configured for each ring stent.

FIG. 10 shows the side view of the prosthesis (10) shown in FIG. 9, such that only the side profile of device (1) according to the invention can be seen. In the prosthesis (10) illustrated, two identical devices (1) are spaced diametrically opposite each other. FIG. 10 clearly shows that terminal ends (6, 6' and 8, 8') project outwardly for engagement with the inner surface of a luminal body vessel after deployment.

FIG. 11 shows detail of the attachment of ring stents (12, 13) to sleeve (11) in the stent graft (10) and also shows detail of the attachment of device (1) to the sleeve (11). As illustrated, the central portion (3, 3') of device (1) has been attached using joining stitches (20A) which also hold the device (1) onto the sleeve (11). Optionally each elongate element is independently attached to sleeve (11) by stitches so that the central portions of both elongate elements lie side-by-side and are aligned. The two elongate elements are then oversewn onto sleeve (11) using joining stitches (20A). Joining stitches (20A) act as a hinge. The two elongate elements of device (1) can rotate relative to each other to facilitate folding of the stent graft (10) for delivery. Other forms of attachment are also possible. Additionally, the location of arms (7, 7') beneath second ring stent (13) occurs prior to the stitching of second ring stent (13) onto sleeve (11). Alternatively, ring stent (13) can be attached to sleeve (11) prior to attachment of each elongate element. In this embodiment, the lower arms will be placed over ring stent (13). Additional stitches (shown as cross-stitch) (21) are located about the junction where lower arms (7, 7') cross underneath second ring stent (13). Thus stitches (21) hold both lower arms (7, 7') and also ring stent (13) securely together on sleeve (11). Additional stitches (22) are located along the length of upper arms (5, 5') and lower arms (7, 7') of the device until the terminal ends thereof. As illustrated terminal ends (6, 6', 8, 8') are free from stitches in order to engage with the inner luminal wall of a body vessel. As illustrated in FIG. 11 arms (5, 5') are shaped to have a kink or bend immediately prior to the terminal ends (6, 6') which prevents the arms slipping within the stitches and presents the terminal ends (6, 6') outwardly when the device (1) is in its deployed mode. Also as illustrated in FIG. 11, lower arms (7, 7') are shaped to have a kink or bend immediately prior to the terminal ends (8, 8') which prevents the arms slipping within the stitches and presents the terminal ends (8, 8') outwardly when the device (1) is in its deployed mode. Stitches (23) hold first ring stent (12) and, separately, second ring stent (13) securely onto the outer surface of sleeve (11). Stitches (20A, 21, 22, 23) may be formed by any convenient means, including hand stitching. Hand stitching has the advantage of accurate stitch placement. Advantageously suture material is used to sew the device (1) and/or ring stents (12, 13) onto sleeve (11). Braided polyester is suitable, though other thread types can also be used. FIG. 11 shows first ring stent (12) and second ring stent (13) formed from multiple strands, for example of nitinol wire.

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A stent graft comprising:
   i. a sleeve having a first end and a second end with a lumen extending therethrough;
   ii. at least two separate ring stents independently attached to the sleeve, a pre-selected distance apart; and
   iii. a device for securing said sleeve to the internal wall of a body lumen, the device comprising at least two separate elongate elements, each said elongate element respectively comprising a central portion with at least one arm extending therefrom, wherein the at least two elongate elements are positioned so that the respective central portions abut and the abutting central portions are joined by a joining element, wherein the joining element is a hinge separate from said elongate elements that enables said elongate elements to rotate, and wherein the terminal end of each arm is adapted to fasten to the internal wall of the body lumen, wherein the device is attached to the sleeve so that it bridges the distance between the ring stents.

2. The stent graft of claim 1, wherein said sleeve is flexible and formed of a woven or knitted fabric.

3. The stent graft of claim 2, wherein the sleeve is formed from a material selected from polyester, polyethylene, polypropylene, ePTFE and PTFE.

4. The stent graft of claim 1 wherein the terminal end of each said arm is adapted to fasten to the internal wall of the body lumen by being hooked or barbed.

5. An implantable prosthesis comprising:
   i. a compliant and substantially fluid impervious tubular sleeve having a proximal end and a distal end with a conduit therethrough;
   ii. a first ring stent formed from multiple winding of wire of a shape memory material, attached to said sleeve at a first location;
   iii. a separate second ring stent formed from multiple windings of wire of a shape memory material independently attached to said sleeve at a second location; and
   iv. a device for securing the prosthesis to the internal wall of a body lumen, the device comprising at least two separate elongate elements, each said elongate element respectively comprising a central portion with at least one arm extending therefrom, wherein the at least two elongate elements are positioned so that the respective central portions abut and the abutting central portions are joined by a joining element, wherein the joining element is a hinge separate from said elongate elements that enables said elongate elements to rotate, and wherein the terminal end of each arm is adapted to fasten to the internal wall of the body lumen; wherein a first portion of each said elongate element is attached to said sleeve at said first location, and wherein a second portion of each said elongate element is attached to said sleeve at said second location.

6. The implantable prosthesis of claim 5, wherein said ring stents are each formed from nitinol wire.

7. The implantable prosthesis of claim 5, wherein one portion of each said elongate element is attached to said sleeve at or adjacent to the location of one ring stent and another portion of each said elongate element is attached to said sleeve at or adjacent to the other said ring stent.

8. The implantable prosthesis of claim 5, wherein said prosthesis comprises a ring stent formed by multiple windings of resilient wire.

9. The implantable prosthesis of claim 8, wherein said device is located between two ring stents, wherein one or both of said ring stents are saddle shaped.

10. The implantable prosthesis of claim 5, wherein said prosthesis comprises at least two of said devices.

11. The implantable prosthesis of claim 10, wherein said at least two said devices are located between two neighbouring ring stents, and are diametrically opposite each other on the sleeve circumference.

12. The implantable prosthesis of claim 5, wherein said prosthesis comprises one or more of said devices located between ring stents at each end of said implantable prosthesis.

13. The implantable prosthesis of claim 5 wherein the terminal end of each said arm is adapted to fasten to the internal wall of the body lumen by being hooked or barbed.

* * * * *